(12) United States Patent
Stange

(10) Patent No.: US 11,925,523 B2
(45) Date of Patent: Mar. 12, 2024

(54) MULTI-SUCTION DENTAL DEVICES, ASSEMBLIES, SYSTEMS, AND METHODS OF USING THE SAME

(71) Applicant: Frederick Stange, New York, NY (US)

(72) Inventor: Frederick Stange, New York, NY (US)

( * ) Notice: Subject to any disclaimer, the term of this patent is extended or adjusted under 35 U.S.C. 154(b) by 319 days.

(21) Appl. No.: 17/342,130

(22) Filed: Jun. 8, 2021

(65) Prior Publication Data

US 2021/0378803 A1 Dec. 9, 2021

Related U.S. Application Data

(60) Provisional application No. 63/036,644, filed on Jun. 9, 2020.

(51) Int. Cl.
*A61C 17/08* (2006.01)
*A61C 17/10* (2006.01)
*A61C 17/12* (2006.01)

(52) U.S. Cl.
CPC ............. *A61C 17/08* (2019.05); *A61C 17/10* (2019.05); *A61C 17/12* (2019.05)

(58) Field of Classification Search
CPC .......... A61C 17/08–135; A61C 17/092; A61B 90/40; A61B 2090/401; A61B 1/24; A61B 1/32
See application file for complete search history.

(56) References Cited

U.S. PATENT DOCUMENTS

| | | | |
|---|---|---|---|
| 4,083,115 A * | 4/1978 | McKelvey | A61C 17/08 433/96 |
| 10,952,831 B1 * | 3/2021 | Dürrstein | A61C 17/096 |
| 10,959,820 B1 * | 3/2021 | Steele | A61C 17/10 |
| 2009/0274991 A1 * | 11/2009 | Black | A61C 17/08 433/93 |
| 2021/0346135 A1 * | 11/2021 | Kerr | A61C 17/092 |
| 2021/0369427 A1 * | 12/2021 | Zhang | A61C 17/08 |
| 2021/0378804 A1 * | 12/2021 | Renne | A61B 1/24 |
| 2022/0192806 A1 * | 6/2022 | Palumbo | A61C 17/08 |

FOREIGN PATENT DOCUMENTS

WO WO-2011057008 A2 * 5/2011 ........... A61C 1/0061

* cited by examiner

*Primary Examiner* — Jacqueline T Johanas
*Assistant Examiner* — Shannel Nicole Belk
(74) *Attorney, Agent, or Firm* — Bryan Cave Leighton Paisner LLP

(57) ABSTRACT

The present disclosure is directed to improved multi-suction dental devices, assemblies, systems and methods and of using the same. The multi-suction dental devices can be configured to suction both liquids and aerosols during dental procedures. Each multi-suction dental device can comprise at least one low-volume evacuation (LVE) suction pathway and at least one high-volume evacuation (HVE) suction pathway.

21 Claims, 12 Drawing Sheets

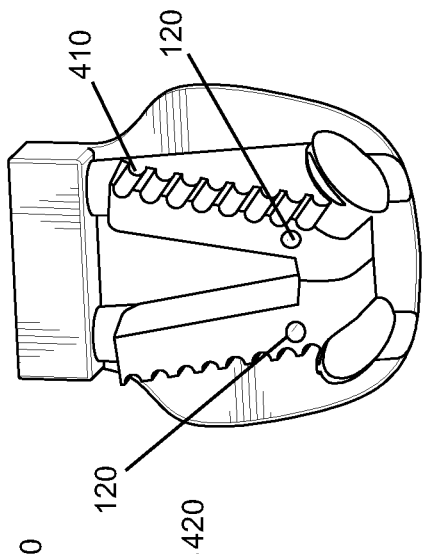
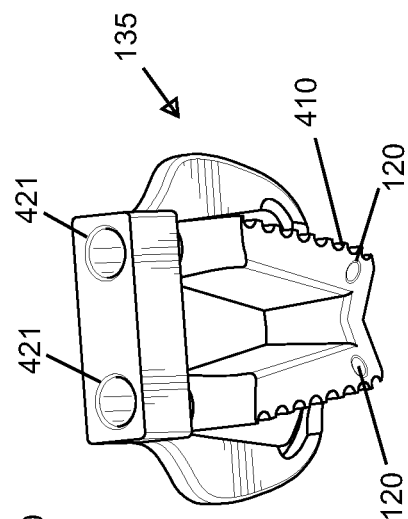
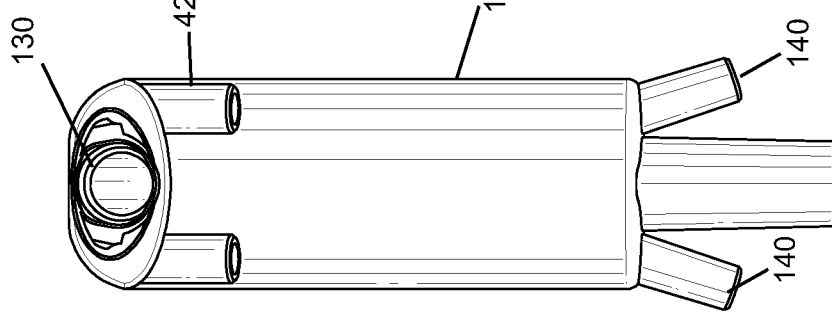
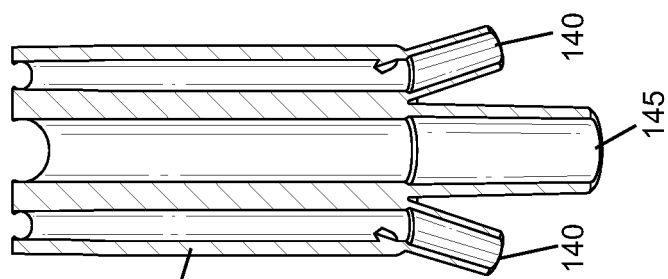
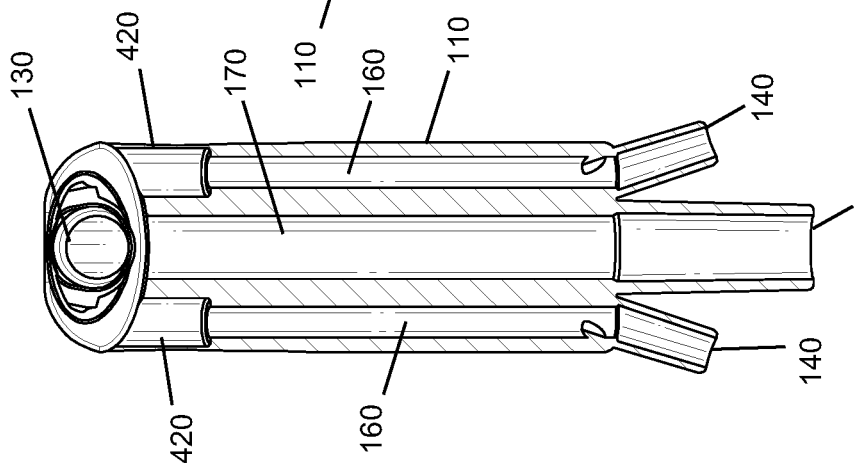

MULTI-SUCTION DENTAL DEVICES, ASSEMBLIES, SYSTEMS, AND METHODS OF USING THE SAME

CROSS-REFERENCE TO RELATED APPLICATIONS

This application claims benefit to U.S. Provisional Patent Application No. 63/036,644 filed on Jun. 9, 2020. The content of the above-identified application is incorporated by reference herein in its entirety.

TECHNICAL FIELD

This disclosure is related to multi-suction dental devices, assemblies, systems, and methods of using the same. The multi-suction dental devices, assemblies, systems, and methods can be configured to simultaneously remove or extract both intraoral liquids and aerosols generated during dental procedures.

BACKGROUND

Many dental procedures utilize intraoral suctioning devices to remove saliva and other liquids from inside of a patient's mouth during a dental procedure. However, these procedures produce aerosols that are not captured by these suctioning devices. The aerosols, which can comprise a cloud of particulate matter and/or liquids, can include a combination of materials originating from the treatment site within a patient's mouth and also from dental unit waterlines (DUWLs). In many cases, the aerosols can include components of saliva, nasopharyngeal secretions, plaque, blood, tooth components and various materials used in the dental procedure (e.g., such as water and/or abrasives for air polishing/abrasion). The aerosols, or components therefore, also may include viruses and/or bacteria which can be dangerous and harmful to dental practitioners and/or other individuals who are exposed to the aerosols. These individuals can be susceptible to various infections caused by these viruses and bacteria.

More recently, several devices have been developed to capture aerosols during a dental procedure. These devices generally fall within two categories: a standalone device that is situated on the ground of a dental exam site which has a suction arm that can be positioned to collect aerosols; and a handheld device that must be held by a dental practitioner during a dental operation to collect aerosols. With respect to the former, these devices require significant office space and cannot be easily moved while a dental procedure is being performed. Moreover, the amount of aerosols collected by these devices is reduced because they cannot be situated in the immediate vicinity of the treatment site (e.g., in or immediately adjacent to a patient's mouth) because doing so would impede the dental practitioner's performance of the dental procedure (e.g., by blocking his or her vision and/or preventing usage of dental instruments). With respect to the latter, these handheld devices must be held by a dental practitioner while performing a dental procedure, which can fatigue the dental practitioner over the course of the dental procedure and encumber the dental practitioner when he or she is required to hold additional dental instruments to perform the dental procedure.

In recent times, COVID-19 (also known as coronavirus disease 2019) is a virus that is rapidly spreading and is of particular concern to both dental personnel and patients alike. There have been major efforts across the world to prevent the spread of this virus. These efforts have resulted in a dramatic decrease in dental visitations and/or appointments due, at least in part, to fears of spreading the virus and government regulations prohibiting dental visitations and/or appointments in certain jurisdictions. The aerosols produced during many dental procedures are of particular concern for spreading the virus.

Various governmental agencies, such as the American Dental Association (ADA), Center for Disease Control and Prevention (CDC), and Occupational Safety and Health Administration (OSHA), have promulgated regulations, recommendations, and guidelines that apply to reducing aerosols during dental procedures. More recently, additional regulations, recommendations, and guidelines have been promulgated which are aimed at preventing spread of COVID-19 and many other types of infections which can be caused by airborne aerosols.

Accordingly, there is a need for improved dental devices, assemblies, systems and methods of using the same which can help eliminate, or at least mitigate, the spread of infections due to aerosols that are created during dental procedures and which do not encumber dental practitioners while performing dental procedures. There is also a need for improved dental devices, assemblies, systems and methods of using the same which can efficiently remove or extract aerosols during a dental procedure without impeding a dental practitioner's performance and without requiring occupying significant floor space in a dental office.

BRIEF DESCRIPTION OF DRAWINGS

To facilitate further description of the embodiments of this disclosure, the following drawings are provided, in which like references are intended to refer to like or corresponding parts, and in which:

FIG. 1H is another exemplary multi-suction dental device in accordance with certain embodiments;

FIG. 1I is a cross-section view of the exemplary multi-suction dental device illustrated in FIG. 1H;

FIG. 1J is a cross-section view of a lower portion of the exemplary multi-suction dental device illustrated in FIG. 1H;

FIG. 1K is a front perspective view of a mouth piece that can be connected to the exemplary multi-suction dental device illustrated in FIG. 1H;

FIG. 1L is a rear perspective view of a bite block that can be connected to the exemplary multi-suction dental device illustrated in FIG. 1H;

Figure 1A:
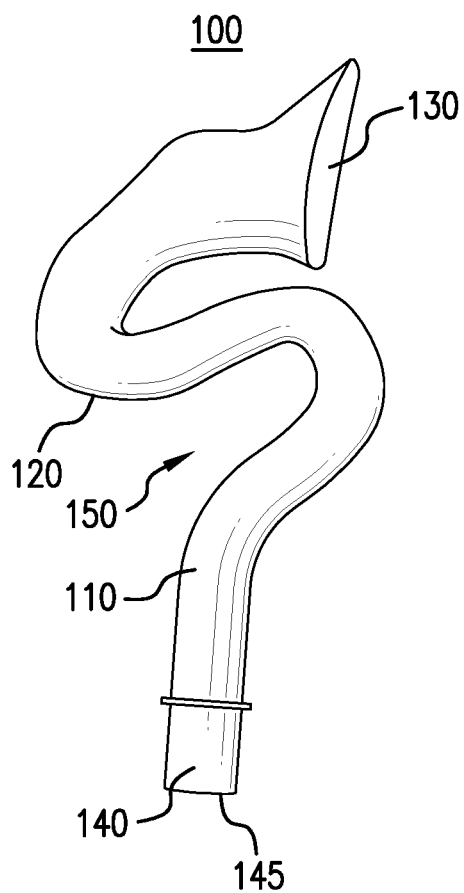
FIG. 1A is an exemplary multi-suction dental device in accordance with certain embodiments.
Figure 1B:
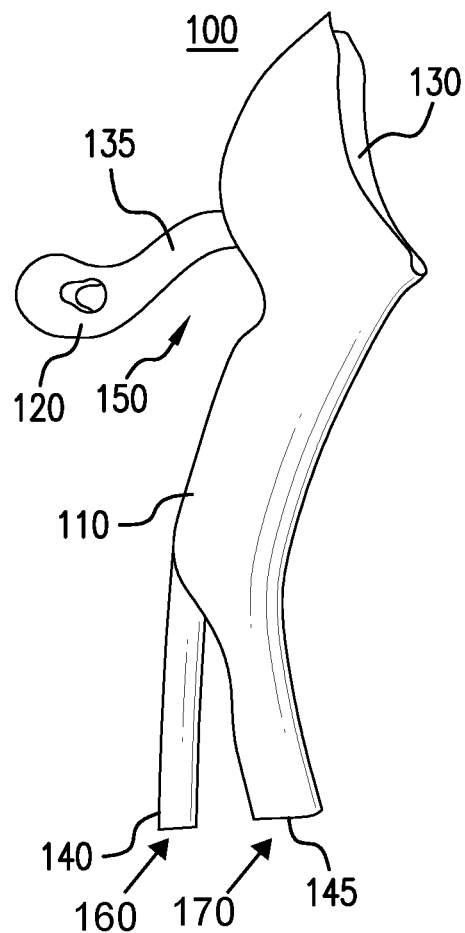
FIG. 1B is another exemplary multi-suction dental device in accordance with certain embodiments.
Figure 1C:
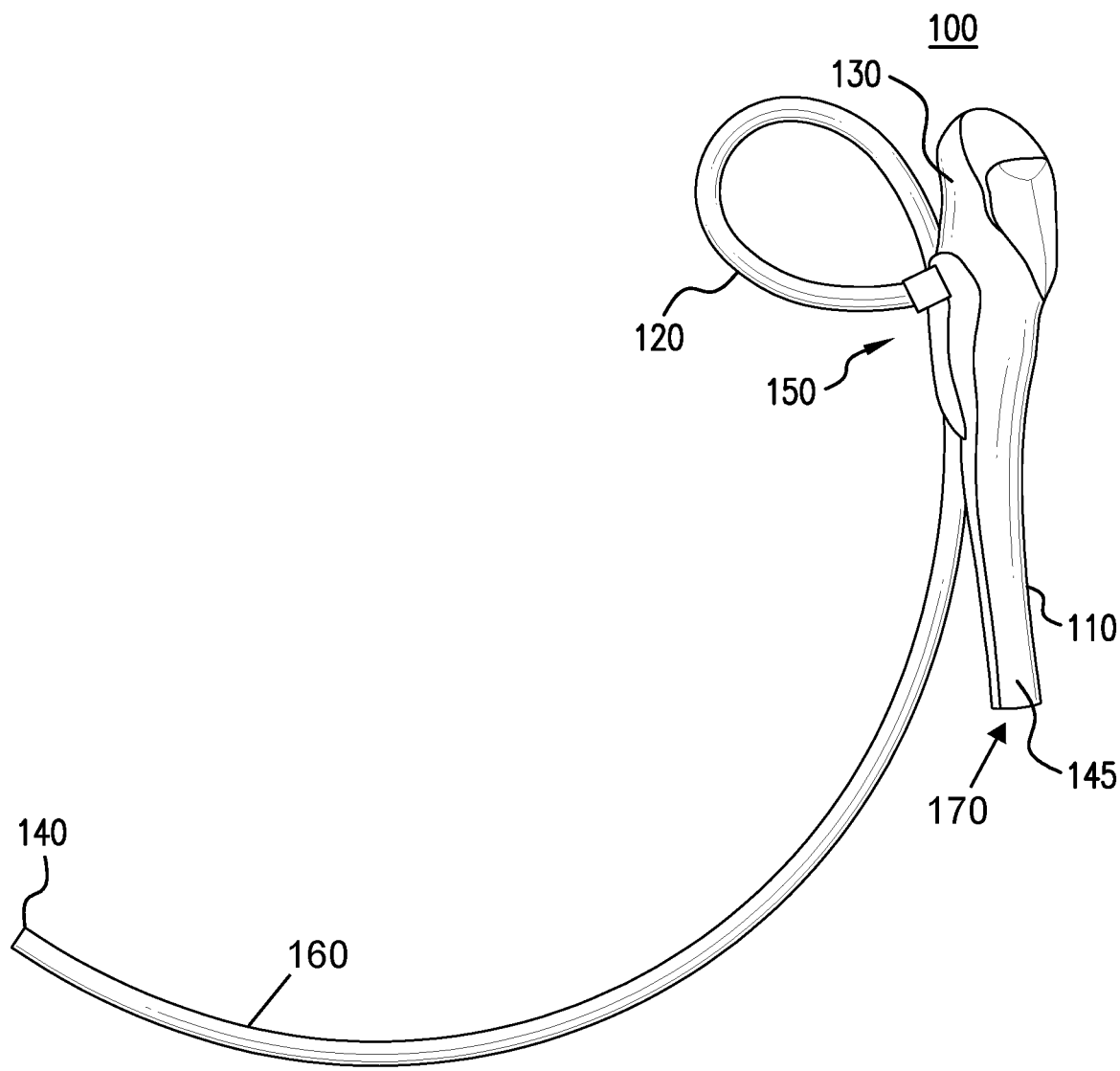
FIG. 1C is another exemplary multi-suction dental device in accordance with certain embodiments.
Figure 1D:
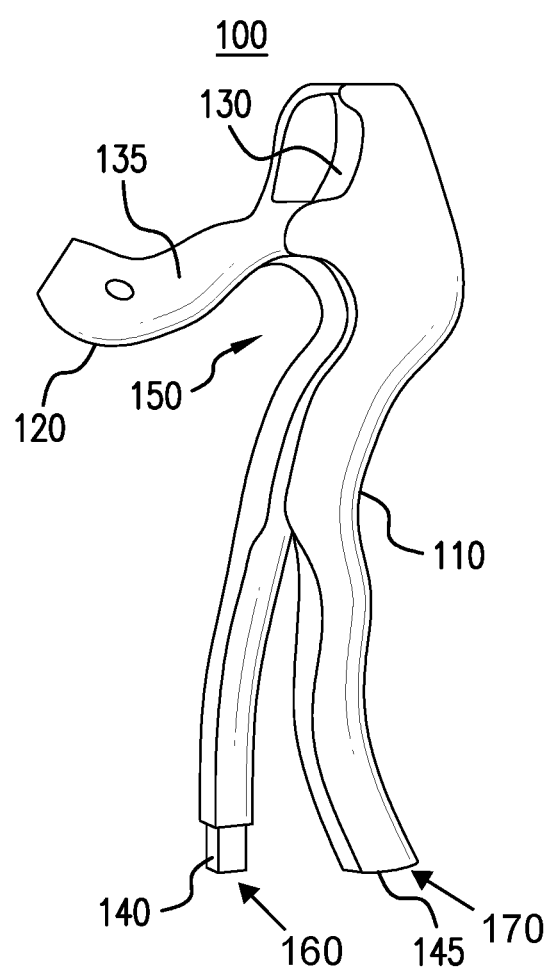
FIG. 1D is another exemplary multi-suction dental device in accordance with certain embodiments.
Figure 1E:
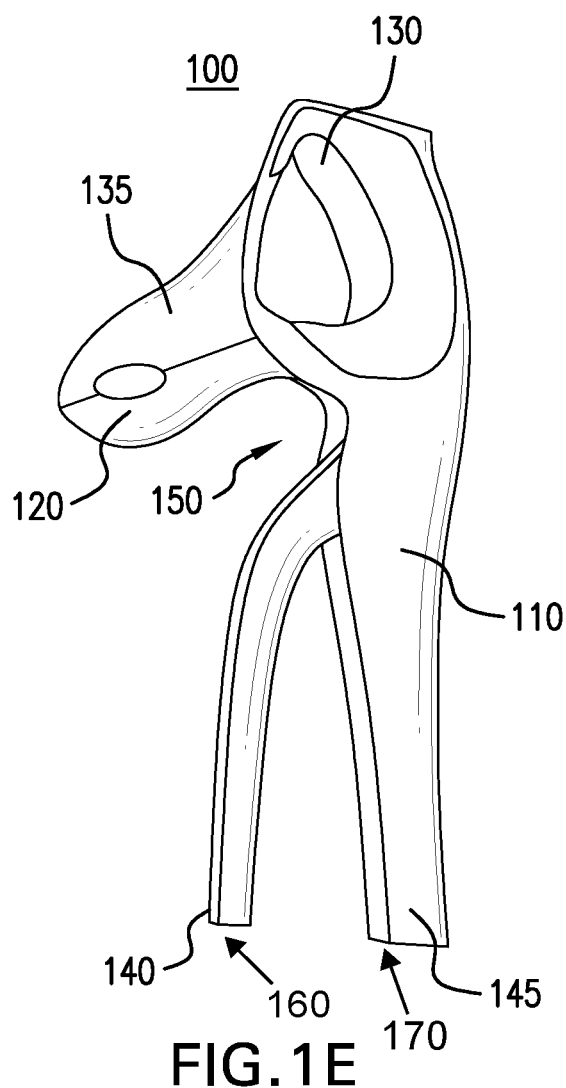
FIG. 1E is another exemplary multi-suction dental device in accordance with certain embodiments.

It should be noted that usage of the terms "patient" and "dental practitioner" throughout this disclosure are not intended to be limiting in any manner whatsoever. Rather, these terms are intended to be interpreted very broadly to cover any individual. For example, while the term "dental practitioner" can include dentists, hygienists, and other individuals who perform services at a dentist office, any individual may perform these functions whether or not they are associated with a dental practice or certified to perform dental services. Similarly, while the term "patient" can include customers of a dental practice, any individual can serve the role of the patient regardless of whether or not they are receiving dental services or located at a dentist office.

DETAILED DESCRIPTION OF EXEMPLARY EMBODIMENTS

The present disclosure relates to improved multi-suction dental devices, assemblies, systems and methods of and using the same. The multi-suction dental devices can be configured to suction both liquids and aerosols during dental procedures. In certain embodiments, each multi-suction dental device can comprise both one or more first suction pathways that provide low-volume evacuation (LVE) for removing liquids during a dental procedure and one or more second suction pathways that provides high-volume evacuation (HVE) for removing aerosols produced during the dental procedure. Some or all of the multi-suction dental device may include an attachment portion that enables the multi-suction dental devices to be comfortably attached or connected to patients (e.g., patients' cheeks and/or lips) during the dental procedures. Additional features of exemplary multi-suction dental devices are described in further detail below.

The multi-suction dental devices described herein can provide various advantages and benefits that overcome some or all of the aforementioned challenges, as well as other challenges not specifically mentioned herein. One significant advantage relates to the fact that a single device is able to simultaneously perform both LVE and HVE in an immediate vicinity of a treatment site during dental procedures. Another advantage is that these devices can include attachment portions that allow the devices to be attached to patients, thus freeing the hands of dental practitioners performing the dental procedures and preventing fatigue resulting from having to hold the devices. Moreover, the ergonomic design and configuration of the devices permits them to be attached to patients in a comfortable manner that does not block the dental practitioner's vision during the dental procedure. Additionally, the multi-suction dental devices are compact in size and do not require any floor space of a dental office to be occupied (which may already be crowded with various devices and multiple dental practitioners during a dental procedure). The multi-suction dental devices can be easily attached and detached from dental assemblies (e.g., from hoses or suction tubes included in traditional dental assemblies), thus permitting them to be stored away when not in use. A further advantage is that the multi-suction dental devices easily can be incorporated into existing dental assemblies (e.g., used with existing suction tubing, ports, and/or vacuum pumps) without having to modify the dental assemblies. Additional advantages and benefits will be apparent to those skilled in the art based on the disclosure provided herein.

Figure 1F:
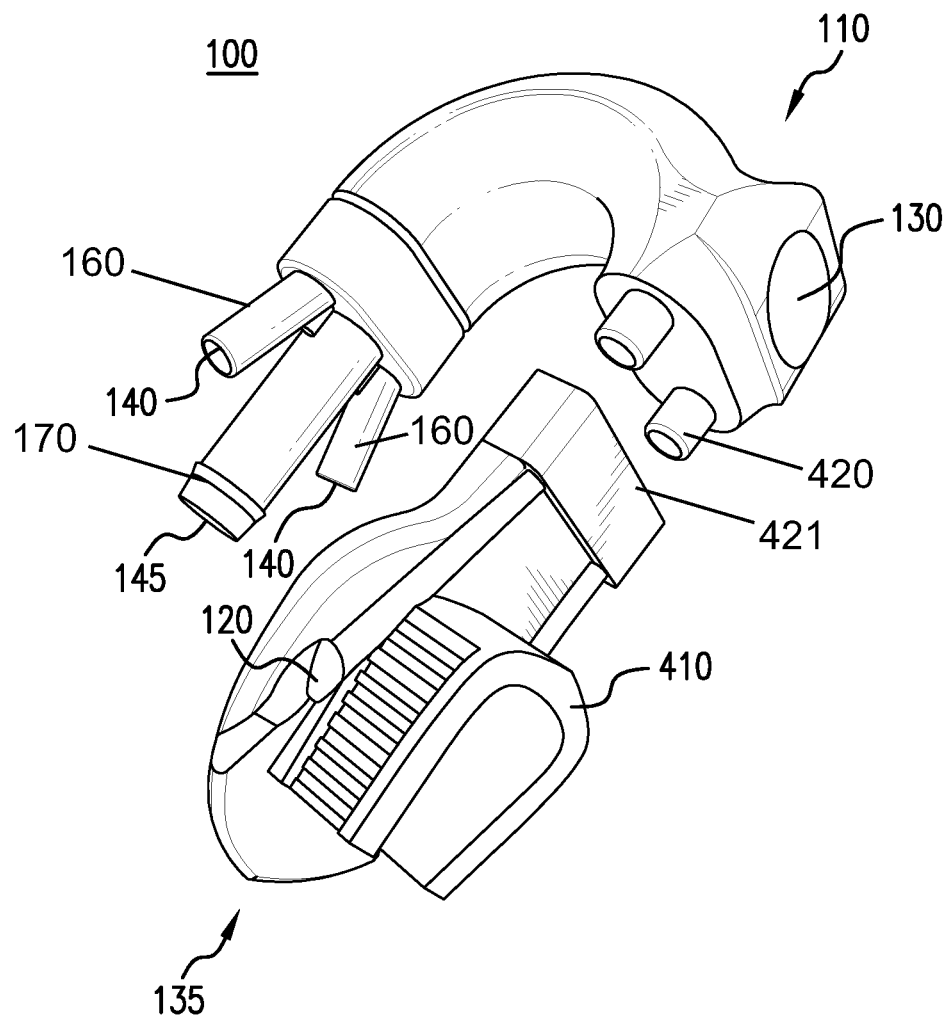
FIG. 1F is another exemplary multi-suction dental device in accordance with certain embodiments.
Figure 1G:
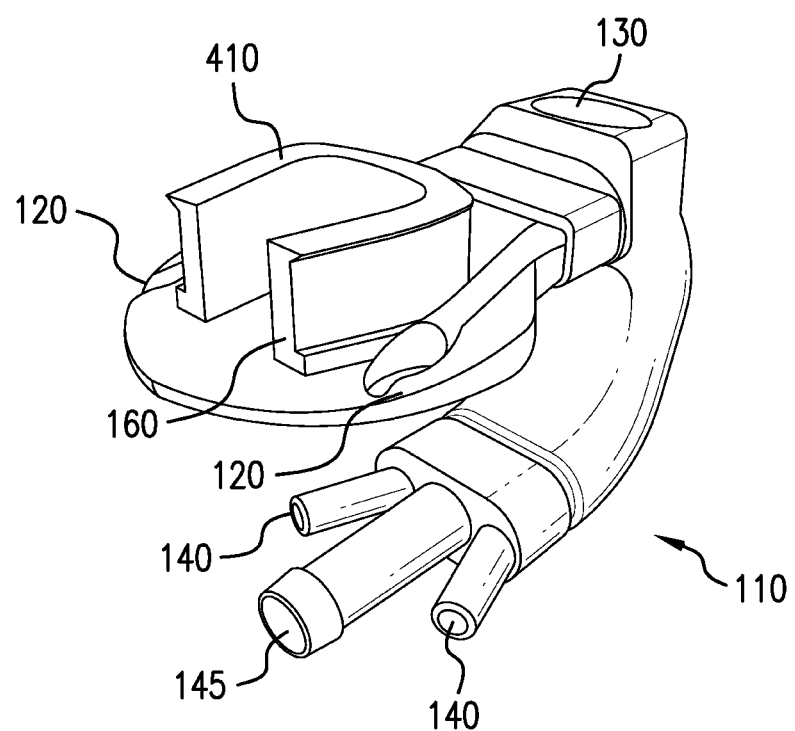
FIG. 1G provides another view of the exemplary multi-suction dental device illustrated in FIG. 1F.
Figure 1M:
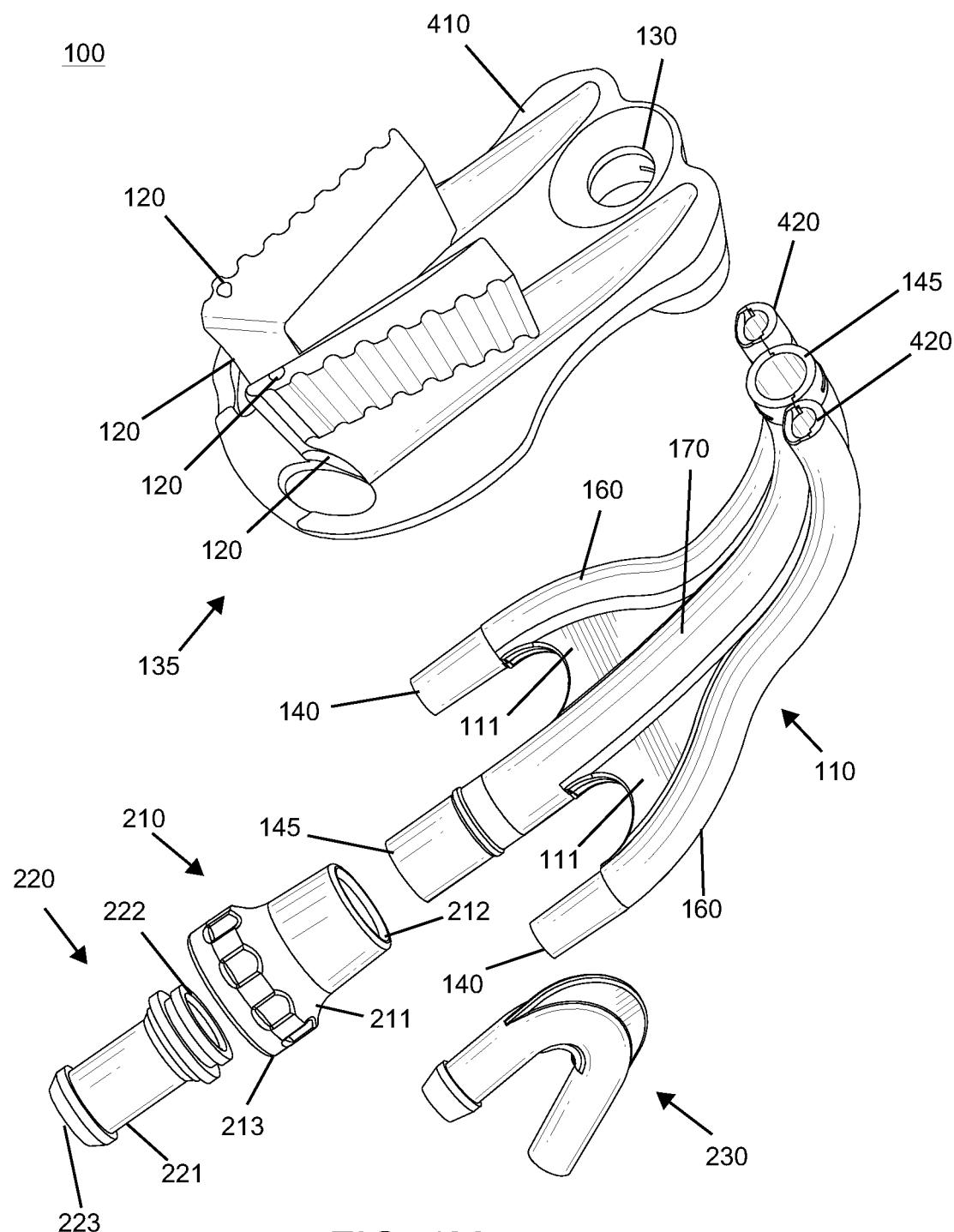
FIG. 1M is a front perspective view of another exemplary multi-suction dental device in accordance with certain embodiments.
Figure 1N:
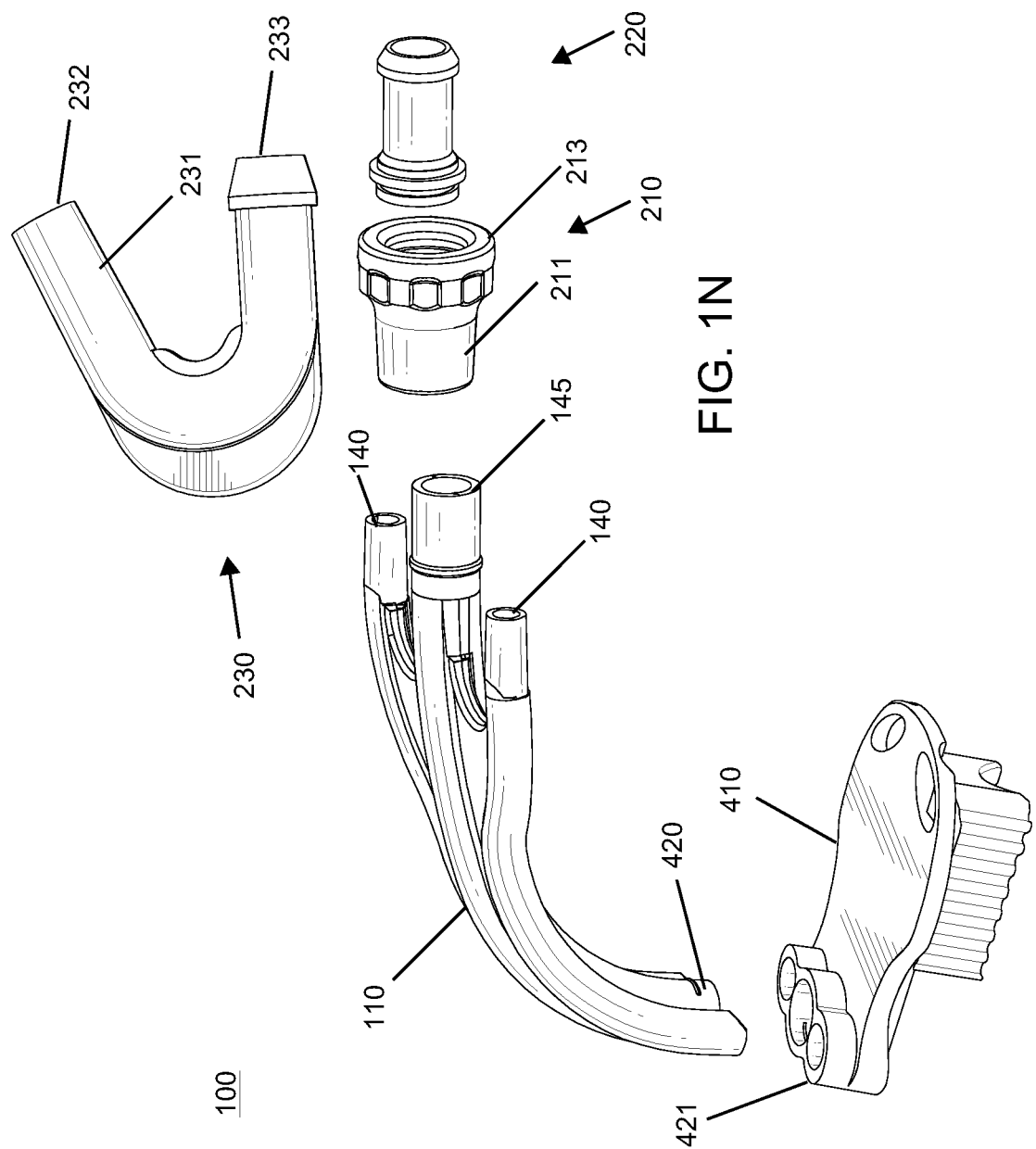
FIG. 1N is a rear perspective view the exemplary multi-suction dental device illustrated in FIG. 1M.

FIGS. 1A-1N disclose exemplary embodiments of multi-suction dental devices 100. Each multi-suction dental device 100 includes a housing 110 (e.g., such as a shell, encasing, or structure) that integrates or combines at least two suction pathways. One or more first suction pathways 160 (also referred to herein as LVE suction pathways 160) can provide low-volume evacuation (LVE) for removing liquids (e.g., saliva, water, abrasives, and/or other liquids) during dental procedures and one or more second suction pathways can provide high-volume evacuation (HVE) for removing aerosols produced during the dental procedures.

Each first suction pathway 160 is defined by a channel or passage beginning at an opening 140 located on the bottom portion of the multi-suction dental device 100 and ending at an LVE bore 120. The opening 140 at the bottom portion of the multi-suction dental device 100 can be configured to receive a tube or hose that is indirectly or directly connected to a vacuum pump (as described in further detail with respect to FIG. 2 below). During a dental procedure, the LVE bore 120 can be situated inside of a patient's mouth and can function to extract or remove liquids from the inside the mouth.

As demonstrated by the embodiments disclosed in FIGS. 1F-1N, some of the multi-suction dental devices 100 can comprise two (or more) first suction pathways 160 for providing LVE during the dental procedure. In some cases, one of the two suction pathways may be activated and used when the multi-suction dental device 100 is used on the left side of a patient's mouth, and the other suction pathway may be activated and used when the multi-suction dental device 100 is used on the right side of the patient's mouth. In some cases, both of the first suction pathways may be simultaneously used and activated during a dental procedure. As explained below, a dental practitioner can switch on/off the suction pathways as desired.

The second suction pathway 170 (also referred to herein as an HVE suction pathway 170) is defined by a channel or passage beginning at an opening 145 located on the bottom portion of the multi-suction dental device 100 and ending at an HVE bore 130. The opening 145 at the bottom portion of the multi-suction dental device 100 can be configured to receive a tube or hose that is indirectly or directly connected to a vacuum pump. During a dental procedure, the HVE bore 130 can be situated near the patients oral cavity (e.g., immediately outside the patient's mouth) and can function to extract or remove aerosols that are generated during a dental procedure. While the exemplary multi-suction dental devices 100 illustrated in FIGS. 1A-1N include a single second suction pathway 170 for providing HVE, it should be recognized that any of the multi-suction dental devices 100 described herein can be modified to include two or more second suction pathways 170, each of which can provide HVE during a dental procedure.

In certain embodiments, the housing 110 of the multi-suction dental device 100 may include an internal wall or structure that separates the first suction pathway(s) 160 from the second suction pathway(s) 170. In many embodiments (e.g., such as depicted in FIGS. 1B, 1C, 1D, 1E, 1F-1G, 1H-L, and 1M-1N), separate tubes or hoses may be connected to each of the first suction pathway(s) 160 and each of the second suction pathway(s) 170. In some embodiments (e.g., such as in FIG. 1A), a single tube or hose can be connected to the multi-suction dental device which provides suctioning for both the first suction pathway 160 and the second suction pathway 170.

The size and configuration of the LVE bore 120 and HVE bore 130 can vary. The size or diameter of the LVE bore 120 can be any size that is appropriate for removing or extracting intraoral liquids, and the size and diameter of the HVE bore 130 can be any size that is appropriate for removing or extracting aerosols during a dental procedure. As shown in the figures, the HVE bore 130 can have a larger diameter than the LVE bore 120 and can extract or remove larger volumes of air than the LVE bore 120 in a given period of time. In certain embodiments, the LVE bore 120 may have a diameter or opening in the range of 5-10 millimeters (mm) and in some cases, 3-6 mm. In certain embodiments, the HVE bore 130 may have a diameter or opening in the range of 8-25 mm and, some cases, 10-15 mm or 11 mm.

Figure 3:
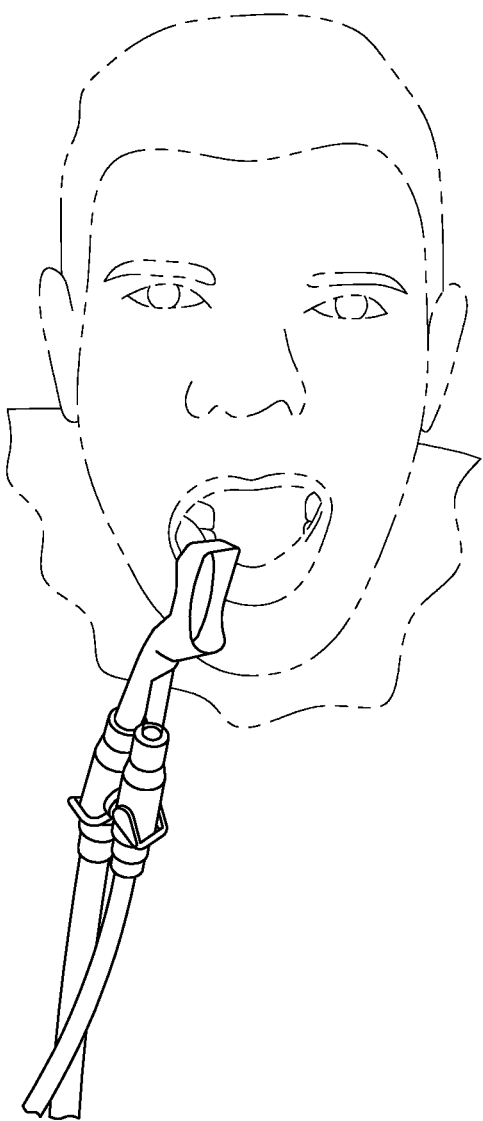
FIG. 3 is an image illustrating how an exemplary multi-suction dental device can be attached to a patient during a dental procedure in accordance with certain embodiments.

The position or location of the LVE bore 120 and HVE bore 130 also can vary. In certain embodiments (e.g., such as those shown in FIGS. 1A, 1B, 1D, and 1E), the LVE bore 120 can be located on the bottom portion of an extension 135 that protrudes laterally from the housing 110 and which partially defines the first suction pathway. The extension portion 135 can be inserted into a patient's mouth (e.g., between the cheek and/or teeth of the patient) during a dental procedure (e.g., as shown in FIG. 3). In certain embodiments (e.g., such as in FIG. 1C), the LVE bore 120 can be placed on the bottom portion of a suction tube that is inserted into a patient's mouth during a dental procedure. In certain embodiments (e.g., such as in FIGS. 1F-1N), the extension portion 135 may be detachable (e.g., such as a detachable bite block component 410) and/or may include more than one LVE bores 120. The location and position of the LVE bore 120 can be varied in other embodiments.

When the extension portion 135 and/or suction tube comprising one or more LVE bores 120 is inserted into the patient's mouth, the structural design of the multi-suction dental devices 100 can situate the HVE bore 130 immediately near the opening of the patient's mouth to collect aerosols (e.g., as shown in FIG. 3). In some cases, the HVE bore 130 may be situated 1-5 inches from the patient's face (directly in front of the mouth region) when the extension portion 135 is inserted into the patient's mouth. In certain embodiments (e.g., such as in FIGS. 1A and 1B) the HVE bore 130 can be situated such that it faces away from the patient's mouth. In other embodiments (e.g., such as those shown in FIGS. 1C, 1D and 1E), the HVE bore 130 can be situated such that it faces towards from the patient's mouth. In further embodiments (e.g., such as those shown in FIGS. 1F-1N), the HVE bore 130 can be situated such that it faces upward, perpendicularly, or laterally with respect to the patient's mouth.

In many cases, the embodiments in FIGS. 1C-1N may be preferable because facing the HVE bore 130 toward or perpendicular with respect to a patient's oral cavity may permit the HVE bore 130 and second suction pathway 170 to capture a higher volume and/or percentage of aerosols generated during dental procedures. The location of the HVE bore 130 in the embodiment FIGS. 1F-1N also provides a further advantage that the hoses or tubes connected to the multi-suction dental device 100 does not interfere with the patient during a dental procedure. As would be understood by a person of ordinary skill in the art, the HVE bore 130 can be situated, or aimed, in locations other than those depicted in the figures.

The size and configuration of the entire multi-suction dental device 100 and/or associated housing 110 also can vary. In certain embodiments, the multi-suction dental device 100 and/or housing 110 can be approximately 5-10 inches (and in some cases 4-6 inches) in length, approximately 1-8 inches (and in some cases 1.5-3 inches) in width, and approximately 0.5-4 inches (and in some cases 0.5-1.5 inches) in depth. As shown in the figures, the lengths, widths, and depths of the multi-suction dental devices 100 and/or associated housings 110 can vary based on the configuration of the devices. The compact sizes of the multi-suction dental devices 100 and/or housings 110 can be advantageous because will not impede a dental practitioner's vision during a dental procedure and they do not occupy floor space in the dental office (which already may be crowded).

Each of the multi-suction dental devices 100 can further include an attachment portion 150 that permits the multi-suction dental devices 100 to be connected or attached to a patient during a dental procedure. In certain embodiments, the attachment portion 150 can include a curved surface (e.g., a U-shaped opening or recess) that is formed by the housing 110 (see FIGS. 1A, 1B, 1D, and 1E), a suction tube (see FIG. 1C), and/or a bite block component 410 (see FIGS. 1F-1N and 4A-4B) associated with the first suction pathway 160 of the multi-suction dental devices 100. The attachment portion 150 can enable the multi-suction dental devices 100 to comfortably rest on the lip or cheek of patients, or to be inserted into the patient's mouth during usage. Moreover, the structure of the multi-suction dental devices 100 is designed such that is does not uncomfortably impact the patient's gums, cheeks, or other intraoral areas when inserted inside the patient's mouth.

As mentioned above, the exemplary embodiment in FIG. 1C includes a suction tube that is used to partially define the first suction pathway. The suction tube is arranged in a loop configuration that can be inserted into a patient's mouth (e.g., between the cheek and teeth of the patient). This embodiment has the added benefit that the loop can serve to prop open a patient's mouth and provide greater access to a treatment site. Moreover, the size of the loop can be adjusted to accommodate patients having different sized mouths.

The exemplary embodiment in FIGS. 1F-1N illustrate embodiments in which the multi-suction dental devices 100 comprise a two-piece or multi-piece housing configuration in which the extension portion 135 is detachable and/or removable. In some embodiments, this can be advantageous because it permits the extension portion 135 which is received in the patient's mouth to be disposable (e.g., such that the extension portion 135 can be replaced each time the multi-suction dental devices 100 are used during a dental procedure). In other cases, the multi-piece housing configuration permits the removable extension portion 135 to be separated for cleaning and/or sterilization.

The multi-suction dental devices 100 permit low-volume evacuation of liquids and high-volume evacuation of aerosols to be performed simultaneously during dental procedures. In certain embodiments, the multi-suction dental devices 100 may include mechanical and/or electronic controls (and/or may be in communication with dental delivery systems and/or other devices that include such controls) that permit a dental practitioner to manipulate and control various functions associated with the multi-suction dental devices 100.

One exemplary control feature may permit the dental practitioners to switch off either (or both) of the low-volume evacuation and high-volume evacuation functions. For example, in some cases, a dental practitioner may only desire to the use low-volume evacuation functionality (and not high-volume evacuation functionality) of the multi-suction dental devices 100, or vice versa. Thus, the controls may permit the dental practitioner to switch off either of these functions during a dental procedure. In some cases, a mechanical control feature (e.g., a dial, switch, and/or button) and/or an electronic control feature (e.g., a selectable option on a touch screen interface and/or graphical user interface) may switch off a suction pathway by closing a valve and/or by inserting a wall or other structure to block the pathway inside of the multi-suction dental devices 100. The multi-suction dental devices 100 (or devices connected thereto) may include other types of control features (e.g., such as mechanical and/or electronic control features that enable dental practitioners to separately adjust the level or strength of the suctioning functions for both the first suction pathway and the second suction pathway).

In certain embodiments (e.g. as illustrated in FIGS. 1F-1N and 4A-4B), the multi-suction dental devices 100 described herein may include a bite block component 410. The bite block component 410 can assist with propping open a patient's mouth and/or jaw during a dental procedure. The structure of the bite block component 410, and its location on the multi-suction dental devices 100, can vary. The structure can generally include any structure that can provide assistance with keeping a patient's mouth and/or jaw open. The location of the bite block component can include any location on the multi-suction dental devices 100 that are intended to be inserted into a patient's mouth.

Figure 4B:
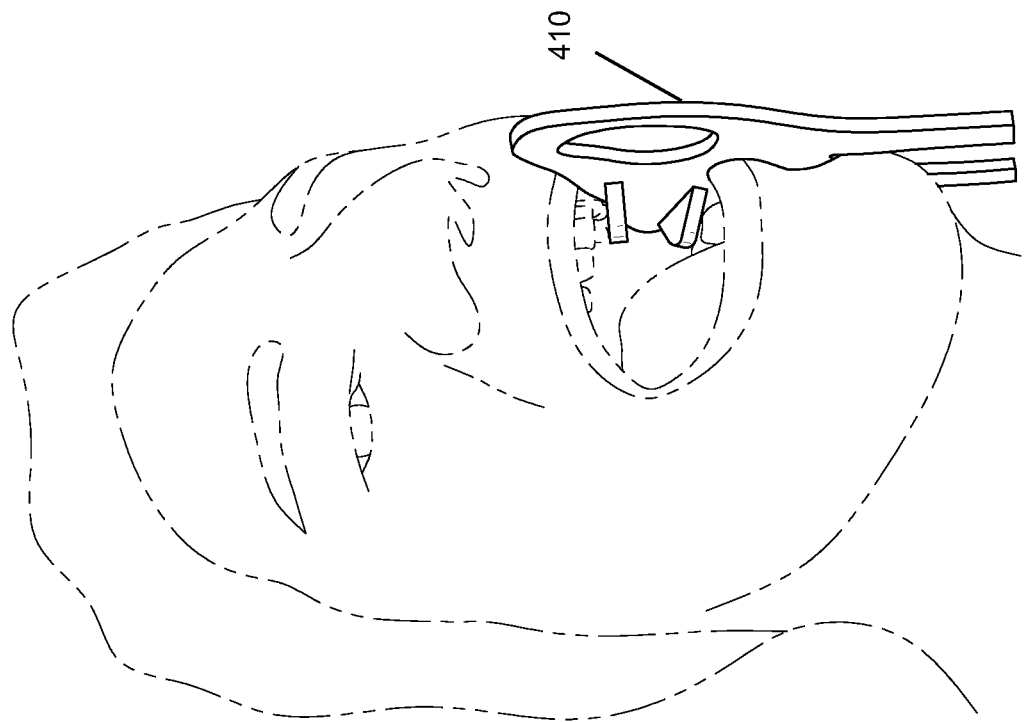
FIG. 4B is an image illustrating an exemplary bite block component being situated into a mouth of an individual in accordance with certain embodiments.
Figure 4A:
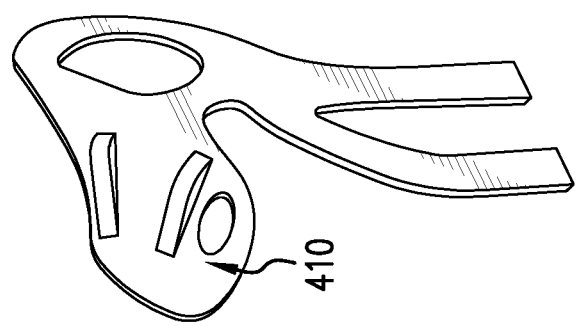
FIG. 4A is an image illustrating an exemplary bite block component in accordance with certain embodiments.

FIGS. 1F-1G, 1H-1L, 1M-1N, and 4A and 4B depict exemplary bite block components 410 in accordance with certain embodiments. In FIGS. 4A and 4B, the bite block component 410 comprises two wall structures that protrude or extend from an extension portion 135 of the multi-suction dental device 100. In certain embodiments (e.g., as shown in 4B), the two wall structures extend or protrude from the side of the extension portion 135 that faces inwardly in the patient's mouth (opposite the side of the extension portion that faces toward the patient's cheek), and situated in an area that permits the patient to bite down on the two wall structures when the multi-suction dental device 100 is in use.

The embodiments disclosed in FIGS. 1F-1G, 1H-1L, and 1M-1N disclose extension portions 135 in which the bite block components 410 comprise U-shaped or V-shaped structures. These U-shaped or V-shape structures extend upward or perpendicularly from a top surface of the extension portions 135. When the extension portions 135 and/or bite block components 410 are inserted into a patient's mouth, these U-shaped or V-shape structures are designed to accommodate the user's palate, and prop open the patient's mouth.

The same or similar bite block components 410 illustrated in FIGS. 1F-1N and 4A-4B can be incorporated into any of the multi-suction dental devices 100 described herein (including any of the multi-suction dental devices 100 illustrated in FIGS. 1A-1E).

In the embodiment illustrated in FIGS. 1F-1G, the HVE bore 130 is located on the housing 110 and situated in a position that is directly in front of a patient's mouth when the extension portion 135 and/or bite block component 410 is received in the patient's mouth. A pair of LVE bores 120 are located on the top surface of the extension portion 135 adjacent to the U-shaped or V-shape structure. The internal configuration of the extension portions 135 include hollow conduits or pathways that form part of the first suction pathways 160, which provide LVE inside the patients' mouths. A pair of connectors 420 (e.g., male connectors) included on the main housing portion enable the extension portion 135 to be physically or mechanically connected to a pair of corresponding connectors 421 (e.g., female connectors) included on the extension portion 135. The connections between the connectors 420 on the main housing portion and the connectors 421 on the extension portion 135 also can be hollow to enable the first suction pathways 160 of the housing 110 to be extended through the extension portion 135 to the LVE bores 120. The connections between the connectors 420 on the main housing portion and the connectors 421 on the extension portion 135 are releasable connections that enable the extension portion 135 to be detached from the housing 110 when desired.

FIGS. 1H-1L disclose a similar embodiment in which the HVE bore 130 is located on the housing 100, and a detachable extension portion 135 includes a pair of LVE bores 120. The same or similar connectors (420, 421) as described above (e.g., which provide both provide a mechanical connection and extend the first suction pathways 160 to the LVE bores 120 via hollow conduits) can be used to connect the extension portion 135 to the housing 110. In this embodiment, the LVE 120 bores 120 are included on a top surface of the bite block component 410 (e.g., on a top surface of the U-shaped or V-shaped structure). FIGS. I and J are cross-section views of a portion of the housing 110 demonstrating how the first suction pathways 160 and second suction pathway 170 include hollow passageways or conduits extending through the housing 110.

FIGS. 1M-1N disclose a similar embodiment in which a first pair of LVE bores 120 are located on a top surface of the bite block component 410, and a second pair of LVE bores are located adjacent to the bite block component 410 (e.g., on a top surface of the extension portion 135). In some cases, all four LVE bores many be connected to via hollow conduits inside of the extension portion 135. In this embodiment, the HVE bore 130 is located on the extension portion 135. The HVE bore 130 is situated in a position on the extension portion 135 that is located immediately outside a patient's mouth when the bite block component 410 (and adjacent portion of the extension portion 135) are inserted inside the patient's mouth.

In this exemplary embodiment, the bottom surface of the extension portion includes three connectors 421 (e.g., female connectors) that are configured to mate with corresponding connectors 420 included on the main housing portion (e.g., via a press fit connection and/or snap connection). Again, the connections formed by the connectors 420 and connectors 421 may enable hollow passageways to extend within the housing 110 from the input bores (i.e., LVE bores 120 and HVE bore 130) included on the extension portion 135 to the openings (i.e., openings 140, 145) on main body portion.

In this exemplary embodiment, a pair of first suction pathways 160 and a second suction pathway 170 are integrated into the main body portion in a manner that minimizes the profile and size of the main body portion. The conduits or structures which provide the first suction pathways 160 and the second suction pathway 170 are directly connected to each other near an upper portion of the main housing that connects to the extension portion 135. The conduits or structures which provide the first suction pathways 160 and the second suction pathway 170 are separated by separator portions 111 near a lower portion of the main housing that directly or indirectly connects to hoses or suction tubes which, in turn, are communication with one or more vacuum systems. This configuration can be advantageous because it minimizes the size of the housing 110 and provides adequate separation of the suction pathways at the locations were they are connected to the hoses or suction tubes.

In some embodiments, the LVE openings 140 located at the bottom of the housing 110 can be configured to directly connect to hoses or suction tubes that provide low-volume evacuation. In some embodiments, the HVE opening(s) 145 also can be configured to directly connect to a hose or suction tube that provides high-volume evacuation. In some embodiments, some or all of the LVE openings 140 and/or HVE openings 145 can be configured to connect to one or more adapters or intermediary connectors which, in turn, connect to the hoses or suction tubes that provide low-volume evacuation and high-volume evacuation.

FIGS. 1M-1N illustrate intermediary connectors that can be used to connect an HVE opening 145 to a hose or suction tube according to some embodiments. The exemplary intermediary connectors include a swivel connector 210 and a hose interface component 220. One end of the swivel connector 210 is configured to connect to the HVE opening 145 and the opposite end is configured to connect to the hose interface component 220. One end of the hose interface component 220 (opposite the end that connects to the swivel connector 210) is configured to connect to a hose or suction tube that provides high-volume evacuation.

In further detail, the exemplary swivel connector 210 includes a body portion 211 that is hollow. In certain embodiments, the exemplary swivel connector 210 can be formed in cylinder or conical shape. An opening 212 at one of the swivel connector 210 is configured to be physically or mechanically connected to the housing 110 at the HVE opening 145 (e.g., using a press fit connection). An opening 213 at the opposite end of the swivel connector 210 is configured to be physically or mechanically connected to an end of the hose interface component 220 (e.g., using corresponding press fit connectors, threaded connectors, and/or other connection mechanisms). The hollow interior of the swivel connector 210 extends from opening 212 to opening 213 to form a conduit that extends through the body portion 211.

In certain embodiments, the swivel connector 210 can to rotate or swivel when the multi-suction dental device 100 is be used during a dental procedure. This can be advantageous because it permits a dental practitioner to position the multi-suction dental device 100 and/or connected hoses in a location that does not obstruct or intervene with administration of the dental procedure.

The hose interface component 220 also includes a body portion 221 that is hollow. In certain embodiments, the body portion 221 can be formed in cylinder shape. An opening 222 at one of the hose interface component 220 is configured to be physically or mechanically connected to the swivel connector 210. An opening 223 at the opposite end of the hose interface component 220 is configured to be physically or mechanically connected to an end of a hose or suction tube (e.g., using corresponding press fit connectors, threaded connectors, and/or other connection mechanisms). The hollow interior of the hose interface component 220 extends from opening 222 to opening 223 to form a conduit that extends through the body portion 221.

In certain embodiments, the dental assemblies disclosed herein may further utilize or include a HVE hand piece adapter 230 that is configured to connect an end of hose or suction tube to a HVE hand piece. For example, some dental chairs or offices may include a HVE handheld device that typically is held by a dental practitioner during administration of certain dental procedures. Holding the device can obstruct or intervene with the dental procedure. When the HVE handheld device is not being used, it may rest on a dental chair hanger that is configured to hold the HVE handheld device, as well as other dental devices.

The HVE hand piece adapter 230 permits these HVE handheld devices to be retrofitted for usage with the multi-suction dental devices 100 described herein. The dental practitioners can leave the HVE handheld device resting on the hanger (or other structure) during administration of the dental procedure, and the HVE hand piece adapter 230 permits the HVE functionality of the HVE handheld devices to be extended to the multi-suction dental devices 100

The HVE hand piece adapter 230 includes a body portion 231 that is hollow. In certain embodiments, the HVE hand piece adapter 230 can be a cylinder formed in U-shape. An opening 232 at one of the HVE hand piece adapter 230 is configured to be physically or mechanically connected to an end of a hose or suction tube (e.g., using corresponding press fit connectors, threaded connectors, and/or other connection mechanisms). An opening 233 at the opposite end of the HVE hand piece adapter 230 is configured to be physically or mechanically connected to a HVE handheld device (e.g., using corresponding press fit connectors, threaded connectors, and/or other connection mechanisms). The hollow interior of the HVE hand piece adapter 230 extends from opening 232 to opening 233 to form a conduit that extends through the body portion 231.

In many cases, the U-shaped body of the HVE hand piece adapter 230 can be formed of a rigid structure (e.g., a rigid polymer or plastic). The combination of the U-shaped body and rigid structure can be beneficial because it allows for connection of the HVE hand piece adapter 230 to a HVE handheld device without blocking the HVE suction pathway or preventing the HVE suction pathway from collapsing.

Figure 2:
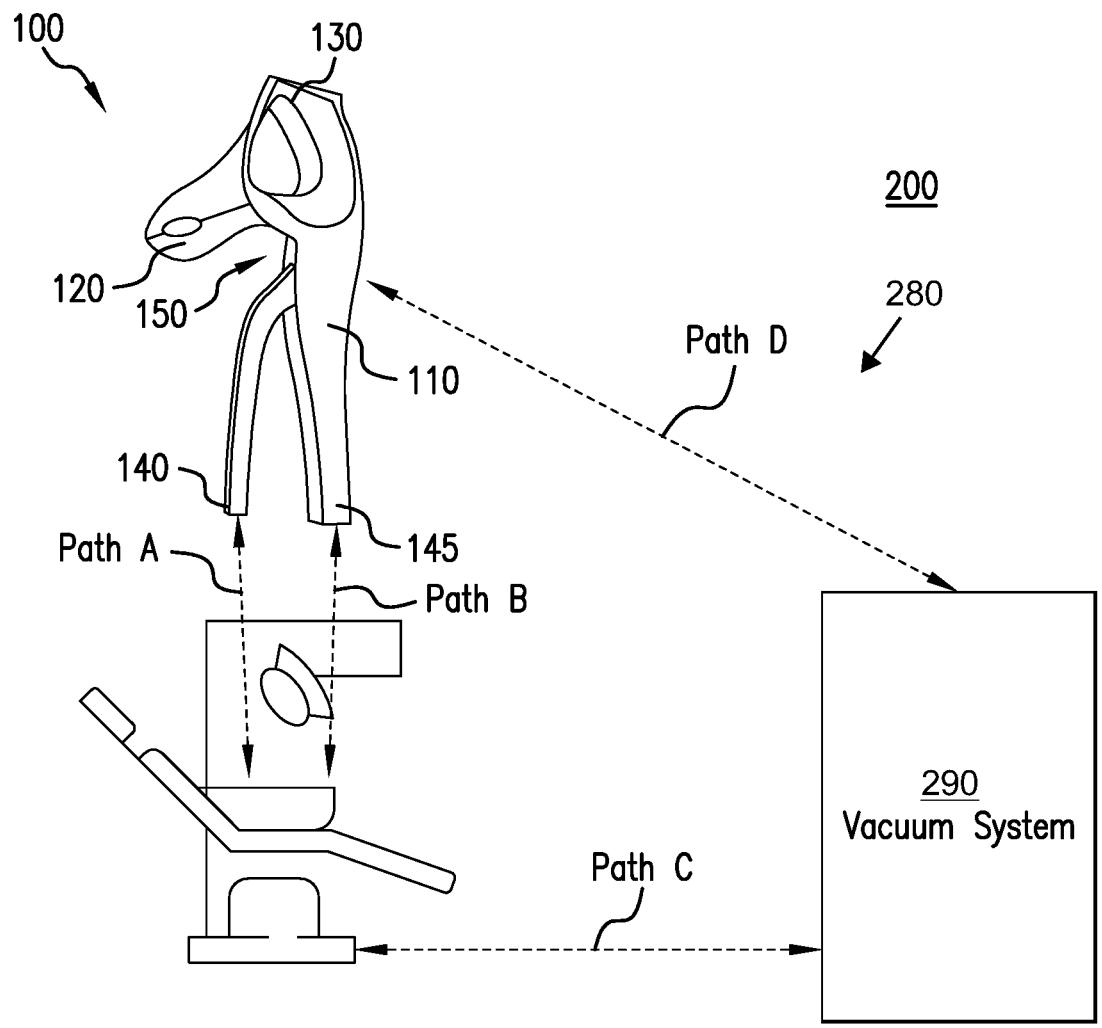
FIG. 2 is an exemplary dental system in accordance with certain embodiments.

FIG. 2 discloses an exemplary system 200 according to certain embodiments. The exemplary system 200 may include one or more multi-suction dental devices 100, one or more dental exam sites 280, and one or more vacuum systems 290. The one or more multi-suction dental devices 100 may include any of the multi-suction dental devices 100 described herein (including any of the multi-suction dental devices 100 illustrated in FIGS. 1A-1N).

The dental exam sites 280 can include any and all tools, instruments, and equipment associated with performing dental procedures or providing dental services. For example, each dental exam site 280 may include any or all of the following: one or more dental chairs, one or more dental operatory lights, x-ray imaging equipment, sterilization equipment, one or more dental hand pieces, one or more HVE handheld devices, one or more dental delivery systems (e.g., which provide a hub for air-powered and/or electric-powered hand pieces and/or other dental instruments), and/or one or more computing systems (e.g., desktop computers, tablets, display screens, etc.).

One or more vacuum systems 290 may be located at the dental exam sites 280 and/or in a dentist office that includes multiple dental exam sites 280. Each vacuum system 290 may include one or more vacuum pumps. The vacuum pumps can provide suctioning functions (e.g., including the LVE and HVE functions) for the multi-suction dental devices 100. In certain embodiments, such as where a dentist office includes multiple dental exam sites 280, a portion of the equipment (e.g., the chairs, delivery systems, and/or hand pieces) at each site may be connected to a central vacuum pump 290 or a plurality of vacuum pumps 290.

In certain embodiments, the multi-suction dental devices 100 can be connected to a dental chair and/or dental delivery system located at a dental exam site 280. For example, separate hoses or tubes may connect a dental chair and/or dental delivery system to one or more openings (140, 145) on the multi-suction dental devices 100 as indicated by Path A and Path B. Path A may represent one or more LVE suction pathways 160 and/or one or more suction tubes or hoses connected to one or more LVE suction pathways 160. Path B may represent one or more HVE pathways 170 and/or one or more suction tubes or hoses connected to one or more LVE suction pathways 170.

The dental chair and/or dental delivery system can, in turn, be connected to a vacuum pump of the vacuum system 290 as indicated by Path C. In certain embodiments, the control features described above (e.g., for switching on/off the suction pathways of the multi-suction dental devices 100 and/or for controlling the strength of the vacuum functions) may be located on (or accessible through) the multi-suction dental devices 100, the dental chairs, the dental delivery systems, the vacuum systems 290 (and/or associated vacuum pumps), and/or computing devices (e.g., desktop computers, laptops, smart phones, mobile devices, etc.) associated with a dental exam site 280.

In certain embodiments, the multi-suction dental devices 100 can be directly connected to a vacuum pump of the vacuum system 290 as indicated by Path D. For example, a hose or tube may directly connect each opening 140 of a multi-suction dental device 100 to a vacuum pump without any intermediary components or connections.

In certain embodiments, the multi-suction dental devices 100 can be utilized by, or incorporated into, existing or traditional dental assemblies located at dental exam sites 280 without having to modify or change the dental assemblies. For example, in some cases, the multi-suction dental devices 100 can be connected to typical hoses or tubes utilized by traditional dental delivery systems, and LVE and HVE suctioning functions can be facilitated using traditional vacuum systems 290 and/or traditional vacuum pumps. Allowing the multi-suction dental devices 100 to be integrated into traditional dental assemblies can be beneficial because it can avoid costs and efforts associated with modifying or replacing equipment at the dental exam sites 280.

In certain embodiments, the dental assemblies located at the dental exam sites 280 can be modified to optimize performance of the multi-suction dental devices 100 and/or the system 200. For example, in certain cases, the ports and tubes/hoses of the system 200 can be modified to optimize the LVE and HVE functions. In one example, the ports and tubes/hoses associated with providing HVE functions may be wider than those used for providing LVE functions. In such cases, the openings (140, 145) on the multi-suction dental devices 100 associated with the second suction pathway may be wider (in comparison to the openings 140 associated with the first suction pathway), along with the corresponding downstream ports located on the equipment (e.g., the dental chairs and/or dental delivery system hubs) at the dental exam site 280 and/or the vacuum pumps of the vacuum system 290. This may facilitate better performance of the HVE functions by allowing greater volumes of air to be suctioned. Other modifications can also be made to optimize performance of the system 200 as well.

Figure 5:
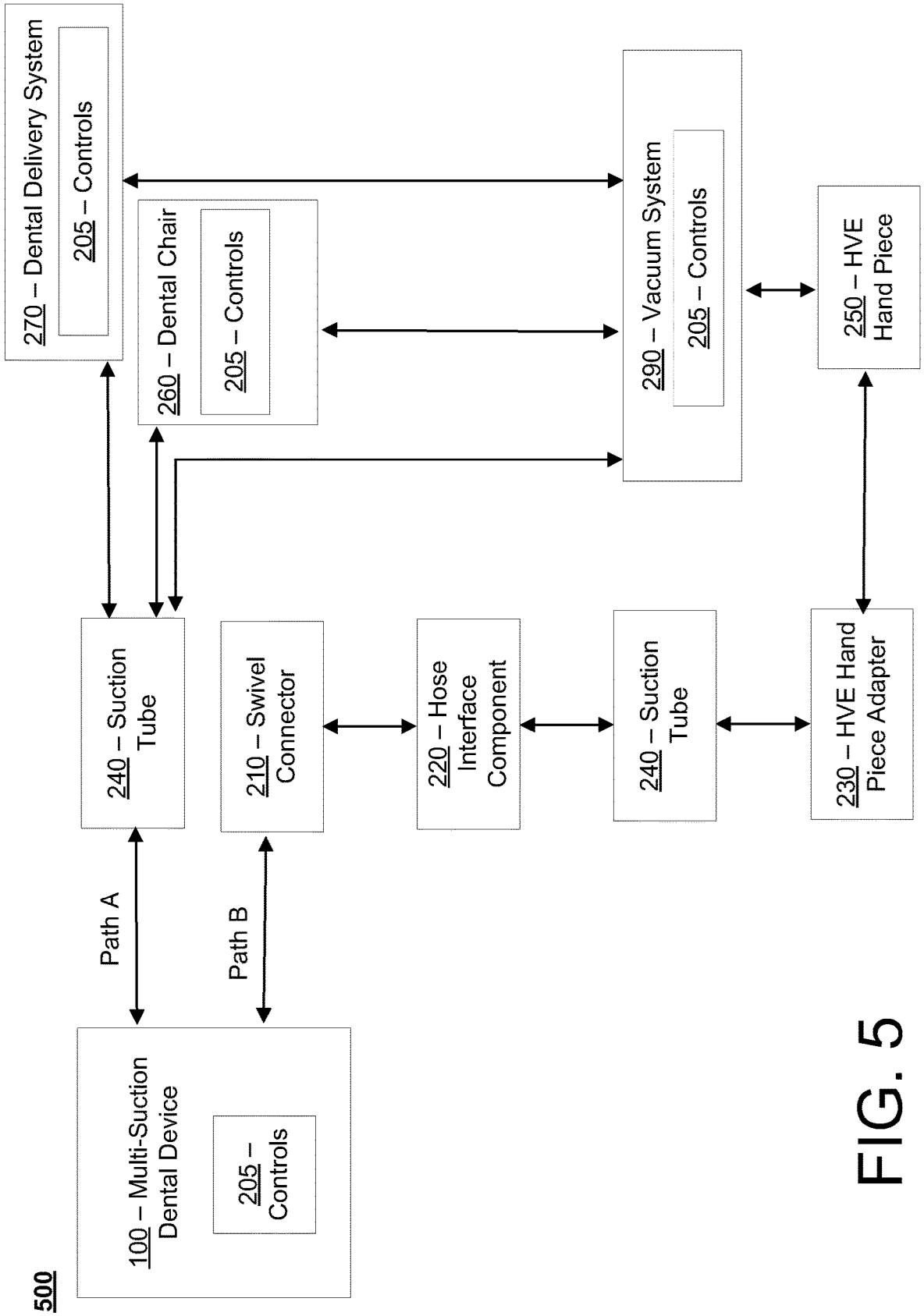
FIG. 5 is a diagram illustrating an exemplary system according to certain embodiments.

FIG. 5 is a diagram illustrating an exemplary system 500 according to certain embodiments. The system 500 demonstrates, inter alia, exemplary schemes for connecting a multi-suction dental device 100 to one or more vacuum systems 290 located an exam site 280. The multi-suction dental device 100 includes one or more LVE suction pathways 160 represented by Path A and one or more HVE suction pathways 170 represented by Path B.

In this embodiment, each of the one or more HVE suction pathways 170 (along Path B) is connected indirectly to a suction tube 240 (e.g., a hose, pipe, or duct that provides HVE suction functionality). For example, a swivel connector 210 can be connected to each of the HVE suction pathways 170 and each swivel connector 210, in turn, can be connected to a hose interface component 220. Each hose interface component 220 connects to an end of a suction tube 240. An opposite end of each suction tube is connected to a HVE hand piece adapter 233. The HVE hand piece adapter 233 is configured to connect to a HVE hand piece 250 that is connected to the one or more vacuum systems 290.

In certain embodiments, each of the one or more LVE suction pathways 160 (along Path A) can be directly connected to a suction tube 240. In other embodiments, each of the one or more LVE suction pathways 160 may be indirectly connected to a suction tube 240 in a similar manner as described above with respect to Path B (via a swivel connector and/or hose interface component).

Each suction tube 240 along Path A can be directly or indirectly connected to the one or more vacuum systems 290. Three exemplary connection schemes for connecting a suction tube 240 along Path A to a vacuum system 290 are shown. A first connection includes a direct connection between the suction tube 240 and the vacuum system 290. A second connection includes a suction tube 240 being connected to a dental chair 260 which, in turn, is directly or indirectly connected to the vacuum system 290. A third connection includes a suction tube 240 being connected to a dental delivery system 270 which, in turn, is directly or indirectly connection to the vacuum system 290. Other types of connection schemes also may be utilized to provide LVE functionality along Path A. Furthermore, Path B can be adapted to accommodate similar connection schemes (e.g., such that the suction tube 240 or adapter 250 along Path B is connected to a dental chair 260 and/or dental delivery system 270 which, in turn, is directly or indirectly connection to the vacuum system 290).

In certain embodiments, the multi-suction dental device 100, dental chair 260, dental delivery system 270, and/or vacuum system 290 can be outfitted with various controls 205 as described above. For example, one or more of these components can include controls 205 (e.g., mechanical and/or electronic controls) for switching on/off the suction pathways of the multi-suction dental devices 100 and/or for controlling the strength of the vacuum functions.

The materials used to manufacture or form the various components (e.g., the housing 110, extension portion 135, bite block component 410, swivel connector 210, hose interface component 220, suction tubes 240, HVE hand piece adapter 230, etc.) of the dental assemblies described herein can vary. Generally speaking, these components can be formed of any suitable material (e.g., polymers, thermoplastics, rubbers, metals, alloys, etc.). In certain embodiments, the housing 110, extension portion 135, hose interface component 220, and HVE hand piece adapter 230 can be formed of a rigid material or rigid plastic, such as acrylonitrile butadiene styrene (ABS), Polypropylene (PP), and/or Polycarbonates (PC). In certain embodiments, the bite block component 410 and swivel connector 210 can be formed from a flexible material, such as rubber. In certain embodiments, the suction tubes 240 may be formed of one or more flexible polymers, such as neoprene polymers and/or other deformable polymers.

It should be noted that any feature described for an embodiment illustrated in the figures and/or described herein can be incorporated into, or combined with, any other embodiment described herein. Moreover, one of ordinary skill in the art would recognize that the shapes, configurations, and/or structures of the multi-suction dental devices 100 can vary, and that the components of the systems (200, 500) can be configured in other arrangements.

In certain embodiments, a multi-suction dental device is provided that comprises: (a) at least one low-volume evacuation (LVE) suction pathway integrated into a housing, wherein: a first end of the at least LVE suction pathway includes at least one LVE bore that is situated on a portion of the housing that is configured to be inserted inside of an individual's mouth during a dental procedure; a second end of the at least one LVE suction pathway includes at least one first opening that is configured to be directly or indirectly connected to one or more suction tubes; and the at least one LVE suction pathway is configured to facilitate extraction of liquid from inside the individual's mouth via the at least one LVE bore during a dental procedure; and (b) at least one high-volume evacuation (HVE) suction pathway integrated into the housing, wherein: a first end of the at least one HVE suction pathway includes at least one HVE bore that is situated in a vicinity outside of the individual's mouth during the dental procedure; a second end of the at least one HVE suction pathway includes at least one second opening that is configured to be directly or indirectly connected to the one or more suction tubes; and the at least one HVE suction pathway is configured to facilitate extraction of aerosol in the vicinity outside of the individual's mouth via the at least one HVE bore during the dental procedure.

In certain embodiments, the housing of the multi-suction dental device comprises a main body portion and a detachable extension portion; the at least LVE suction pathway includes a first LVE suction pathway that includes a first LVE bore located on the extension portion; the at least LVE suction pathway includes a second LVE suction pathway that includes a second LVE bore located on the extension portion; the at least HVE suction pathway includes a first LVE suction pathway that includes a first HVE bore located on the extension portion; the first LVE suction pathway includes a first channel that extends within the housing and through both the main body portion and the detachable extension portion; the second LVE suction pathway includes a second channel that extends within the housing and through both the main body portion and the detachable extension portion; and the first HVE suction pathway includes a third channel that extends within the housing and through both the main body portion and the detachable extension portion.

In certain embodiments, a dental assembly is provided that comprises: a multi-suction dental device that includes: at least one low-volume evacuation (LVE) suction pathway integrated into a housing of the multi-suction dental device, wherein the at least one LVE suction pathway is configured to facilitate extraction of liquid via at least one LVE bore included on the multi-suction dental device; and at least one high-volume evacuation (HVE) suction pathway integrated into the housing of the multi-suction dental device, wherein the at least one HVE suction pathway is configured to facilitate extraction of aerosol via at least one HVE bore included on the multi-suction dental device; and one or more openings that enable connection of one or more suction tubes to the multi-suction dental device.

While various novel features of the invention have been shown, described, and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps in the methods may be carried out in different orders in many cases where such may be appropriate. Those skilled in the art will recognize, based on the above disclosure and an understanding therefrom of the teachings of the invention and the general functionality provided by and incorporated therein, may vary in different embodiments of the invention. Accordingly, the description of system components are for illustrative purposes to facilitate a full and complete understanding and appreciation of the various aspects and functionality of particular embodiments of the invention as realized in system and method embodiments thereof. Those skilled in the art will appreciate that the invention can be practiced in other than the described embodiments, which are presented for purposes of illustration and not limitation. Variations, modifications, and other implementations of what is described herein may occur to those of ordinary skill in the art without departing from the spirit and scope of the present invention.

What is claimed is:

1. A multi-suction dental device comprising:
   at least one low-volume evacuation (LVE) suction pathway integrated into a housing, wherein:
      a first end of the at least one LVE suction pathway includes at least one LVE bore that is situated on a portion of the housing that is configured to be inserted inside of an individual's mouth during a dental procedure;
      a second end of the at least one LVE suction pathway includes at least one first opening that is configured to be directly or indirectly connected to one or more suction tubes;
      the at least one LVE suction pathway is configured to facilitate extraction of liquid from inside the individual's mouth via the at least one LVE bore during the dental procedure;
      the housing includes a bite block component; and
      the at least one LVE bore is located on or adjacent to the bite block component; and
   at least one high-volume evacuation (HVE) suction pathway integrated into the housing, wherein:
      a first end of the at least one HVE suction pathway includes at least one HVE bore that is configured to be situated in a vicinity outside of the individual's mouth during the dental procedure;
      a second end of the at least one HVE suction pathway includes at least one second opening that is configured to be directly or indirectly connected to the one or more suction tubes; and
      the at least one HVE suction pathway is configured to facilitate extraction of aerosol in the vicinity outside of the individual's mouth via the at least one HVE bore during the dental procedure.

2. The multi-suction dental device of claim 1, wherein:
   the at least one LVE suction pathway includes at least one channel or passage within the housing connecting the at least one LVE bore to the at least one first opening; and
   the at least one HVE suction pathway includes at least one channel or passage within the housing connecting the at least one HVE bore to the at least one second opening.

3. The multi-suction dental device of claim 1, wherein:
the housing includes a main body portion and an extension portion; and
the at least one LVE bore is situated on the extension portion.

4. The multi-suction dental device of claim 3, wherein:
the at least one LVE bore includes a first LVE bore and a second LVE bore;
the first LVE bore is situated in a first position on the extension portion that permits extraction of liquid from a side of the individual's mouth;
the second LVE bore is situated in a second position on the extension portion that permits extraction of liquid from an opposite side of the individual's mouth.

5. The multi-suction dental device of claim 3, wherein the at least one HVE bore is situated on the bite block component included on the extension portion.

6. The multi-suction dental device of claim 1, wherein:
the housing includes a main body portion and a detachable extension portion;
the main body portion includes one or more first connectors;
the detachable extension portion includes one or more second connectors; and
the one or more first connectors and one or more second connectors enable the extension portion to be detached from the main body portion.

7. The multi-suction dental device of claim 6, wherein:
the at least one LVE bore and the at least one HVE bore are located on the detachable extension portion; and
the at least one LVE suction pathway and the at least one HVE suction pathway extend through the main body portion and the detachable extension portion when the detachable extension portion is connected to the main body portion.

8. The multi-suction dental device of claim 1, wherein:
a first mechanical or electronic control enables suctioning via the at least one LVE suction pathway to be switched on and off; and
a second mechanical or electronic control enables suctioning via the at least one HVE suction pathway to be switched on and off.

9. The multi-suction dental device of claim 1, wherein:
the housing comprises a main body portion and a detachable extension portion;
the at least one LVE suction pathway includes a first LVE suction pathway that includes a first LVE bore located on the extension portion;
the at least one LVE suction pathway includes a second LVE suction pathway that includes a second LVE bore located on the extension portion;
the at least one HVE suction pathway includes a first LVE suction pathway that includes a first HVE bore located on the extension portion;
the first LVE suction pathway includes a first channel that extends within the housing and through both the main body portion and the detachable extension portion;
the second LVE suction pathway includes a second channel that extends within the housing and through both the main body portion and the detachable extension portion; and
the first HVE suction pathway includes a third channel that extends within the housing and through both the main body portion and the detachable extension portion.

10. A dental assembly comprising:
a multi-suction dental device that includes:
at least one low-volume evacuation (LVE) suction pathway integrated into a housing of the multi-suction dental device, wherein the at least one LVE suction pathway is configured to facilitate extraction of liquid via at least one LVE bore included on the multi-suction dental device, the housing includes a bite block component, and the at least one LVE bore is located on or adjacent to the bite block component; and
at least one high-volume evacuation (HVE) suction pathway integrated into the housing of the multi-suction dental device, wherein the at least one HVE suction pathway is configured to facilitate extraction of aerosol via at least one HVE bore included on the multi-suction dental device; and
one or more openings that enable connection of one or more suction tubes to the multi-suction dental device.

11. The dental assembly of claim 10, wherein:
the at least one LVE suction pathway includes at least one channel or passage within the housing of the multi-suction dental device connecting the at least one LVE bore to at least one of the one or more openings; and
the at least one HVE suction pathway includes at least one channel or passage within the housing of the multi-suction dental device connecting the at least one HVE bore to at least one of the one or more openings.

12. The dental assembly of claim 10, wherein:
the housing includes a main body portion and a detachable extension portion;
the main body portion includes one or more first connectors;
the detachable extension portion includes one or more second connectors; and
the one or more first connectors and one or more second connectors enable the detachable extension portion to be detached from the main body portion; and
the at least one LVE bore or the at least one HVE bore are located on the detachable extension portion.

13. The dental assembly of claim 10, further comprising:
a first mechanical or electronic control that enables suctioning via the at least one LVE suction pathway to be switched on and off; or
a second mechanical or electronic control that enables suctioning via the at least one HVE suction pathway to be switched on and off.

14. The dental assembly of claim 10, wherein:
the housing includes a main body portion and an extension portion; and
the at least one LVE bore and the at least one HVE bore are located on the extension portion.

15. The dental assembly of claim 10, further comprising:
one or more vacuum systems directly or indirectly connected to the one or more suction tubes, wherein the one or more vacuum systems are configured to perform suctioning along the at least one LVE suction pathway and the at least one HVE suction pathway.

16. The dental assembly of claim 10, further comprising:
at least one swivel connector, wherein the at least one swivel connector is configured to be connected to at least one of the one or more openings.

17. The dental assembly of claim 16, wherein the at least one swivel connector is formed of a flexible material and permits the at least one swivel connector to be deformed or bend.

18. The dental assembly of claim 16, further comprising:
at least one suction tube interface component, wherein a first end of the at least one suction tube interface component is configured to be connected to the at least one swivel connector and a second end of the at least one suction tube interface is configured to be connected to at least one of the one or more suction tubes.

19. A multi-suction dental device comprising:
at least one low-volume evacuation (LVE) suction pathway integrated into a housing, wherein:
  a first end of the at least one LVE suction pathway includes at least one LVE bore that is situated on a portion of the housing that is configured to be inserted inside of an individual's mouth during a dental procedure;
  a second end of the at least one LVE suction pathway includes at least one first opening that is configured to be directly or indirectly connected to one or more suction tubes; and
  the at least one LVE suction pathway is configured to facilitate extraction of liquid from inside the individual's mouth via the at least one LVE bore during the dental procedure; and
at least one high-volume evacuation (HVE) suction pathway integrated into the housing, wherein:
  a first end of the at least one HVE suction pathway includes at least one HVE bore that is_configured to be situated in a vicinity outside of the individual's mouth during the dental procedure;
  a second end of the at least one HVE suction pathway includes at least one second opening that is configured to be directly or indirectly connected to the one or more suction tubes;
  the at least one HVE suction pathway is configured to facilitate extraction of aerosol in the vicinity outside of the individual's mouth via the at least one HVE bore during the dental procedure;
  the housing includes a main body portion and an extension portion;
  the at least one LVE bore is situated on the extension portion; and
  the at least one HVE bore is situated on a bite block component included on the extension portion.

20. A multi-suction dental device comprising:
at least one low-volume evacuation (LVE) suction pathway integrated into a housing, wherein:
  a first end of the at least one LVE suction pathway includes at least one LVE bore that is situated on a portion of the housing that is configured to be inserted inside of an individual's mouth during a dental procedure;
  a second end of the at least one LVE suction pathway includes at least one first opening that is configured to be directly or indirectly connected to one or more suction tubes; and
  the at least one LVE suction pathway is configured to facilitate extraction of liquid from inside the individual's mouth via the at least one LVE bore during the dental procedure; and
at least one high-volume evacuation (HVE) suction pathway integrated into the housing, wherein:
  a first end of the at least one HVE suction pathway includes at least one HVE bore that is configured to be situated in a vicinity outside of the individual's mouth during the dental procedure;
  a second end of the at least one HVE suction pathway includes at least one second opening that is configured to be directly or indirectly connected to the one or more suction tubes; and
  the at least one HVE suction pathway is configured to facilitate extraction of aerosol in the vicinity outside of the individual's mouth via the at least one HVE bore during the dental procedure;
wherein:
  the housing includes a main body portion and a detachable extension portion;
  the main body portion includes one or more first connectors;
  the detachable extension portion includes one or more second connectors;
  the one or more first connectors and one or more second connectors enable the extension portion to be detached from the main body portion;
  the at least one LVE bore and the at least one HVE bore are located on the detachable extension portion; and
  the at least one LVE suction pathway and the at least one HVE suction pathway extend through the main body portion and the detachable extension portion when the detachable extension portion is connected to the main body portion.

21. A multi-suction dental device comprising:
at least one low-volume evacuation (LVE) suction pathway integrated into a housing, wherein:
  a first end of the at least one LVE suction pathway includes at least one LVE bore that is situated on a portion of the housing that is configured to be inserted inside of an individual's mouth during a dental procedure;
  a second end of the at least one LVE suction pathway includes at least one first opening that is configured to be directly or indirectly connected to one or more suction tubes;
  the at least one LVE suction pathway is configured to facilitate extraction of liquid from inside the individual's mouth via the at least one LVE bore during the dental procedure; and
at least one high-volume evacuation (HVE) suction pathway integrated into the housing, wherein:
  a first end of the at least one HVE suction pathway includes at least one HVE bore that is configured to be situated in a vicinity outside of the individual's mouth during the dental procedure;
  a second end of the at least one HVE suction pathway includes at least one second opening that is configured to be directly or indirectly connected to the one or more suction tubes; and
  the at least one HVE suction pathway is configured to facilitate extraction of aerosol in the vicinity outside of the individual's mouth via the at least one HVE bore during the dental procedure;
wherein:
the housing comprises a main body portion and a detachable extension portion;
the at least one LVE suction pathway includes a first LVE suction pathway that includes a first LVE bore located on the extension portion;
the at least one LVE suction pathway includes a second LVE suction pathway that includes a second LVE bore located on the extension portion;
the at least one HVE suction pathway includes a first LVE suction pathway that includes a first HVE bore located on the extension portion;

the first LVE suction pathway includes a first channel that extends within the housing and through both the main body portion and the detachable extension portion;

the second LVE suction pathway includes a second channel that extends within the housing and through both the main body portion and the detachable extension portion; and the first HVE suction pathway includes a third channel that extends within the housing and through both the main body portion and the detachable extension portion.

* * * * *